United States Patent [19]

Steigmeier et al.

[11] Patent Number: 4,598,997
[45] Date of Patent: Jul. 8, 1986

[54] APPARATUS AND METHOD FOR DETECTING DEFECTS AND DUST ON A PATTERNED SURFACE

[75] Inventors: Edgar F. Steigmeier, Hedingen; Heinrich Auderset, Horgen, both of Switzerland

[73] Assignee: RCA Corporation, Princeton, N.J.

[21] Appl. No.: 399,290

[22] Filed: Jul. 19, 1982

[30] Foreign Application Priority Data

Feb. 15, 1982 [GB] United Kingdom ................ 8204340

[51] Int. Cl.[4] ............................................. G01N 21/89
[52] U.S. Cl. ..................................... 356/237; 250/572
[58] Field of Search ................ 356/237, 446; 250/562, 250/563, 572

[56] References Cited

U.S. PATENT DOCUMENTS

| | | | |
|---|---|---|---|
| 4,030,835 | 6/1977 | Firester et al. | 250/572 X |
| 4,197,011 | 4/1980 | Hudson | 356/237 X |
| 4,202,627 | 5/1980 | Suzki et al. | 356/446 X |
| 4,314,763 | 2/1982 | Steigmeier et al. | 356/237 |
| 4,391,524 | 7/1983 | Steigmeier et al. | 356/237 X |
| 4,423,331 | 12/1983 | Koizumi et al. | 356/446 X |

Primary Examiner—Davis L. Willis
Assistant Examiner—Matthew W. Koren
Attorney, Agent, or Firm—Birgit E. Morris; Donald S. Cohen

[57] ABSTRACT

Apparatus for detecting defects and dust on patterned surfaces, such as patterned wafers, or grooved video disks, utilizes a scanning laser that provides light scattered by defects and dust. The scattered light is detected substantially free of diffracted beams from the pattern by a mask having apertures arranged to pass to the detector only scattered light and to block diffracted light and specular reflections.

8 Claims, 17 Drawing Figures

Fig. 1.

PRIOR ART

THRESHOLD I = 754
Δ = 10

Fig. 8c

THRESHOLD I = 704
Δ = 60

APPARATUS AND METHOD FOR DETECTING DEFECTS AND DUST ON A PATTERNED SURFACE

This invention is directed to detecting defects and dust on a patterned surface such as a patterned wafer or grooved video disc.

BACKGROUND OF THE INVENTION

Silicon wafers useful in the manufacture of semiconductor devices require close scrutiny to detect defects as soon as possible in the manufacturing process. Several apparatus are known in the art for detecting microscopic defects on the surface or near the surface of such devices. One such apparatus as described as U.S. Pat. No. 4,314,763 issued on Feb. 9, 1982 to E. F. Steigmeier, et al. utilizes a laser beam that is scanned over the surface of a wafer and includes means for detecting scattered radiation from the wafer surface. The specular reflection is blocked from the detection device by suitable arrangement of the lenses and spatial filters. If the surface of the wafer has an imperfection such as dirt, hills, scratches and the like, the laser beam will be scattered from the imperfection. There are also scattering processes such as Raman scattering, etc., which occur, but the intensity of the light due to such scattering effects is usually negligible. The scattered light from the wafer is collected from about the main axis of the lens and is focused on a detector. The scattered light is converted to electrical impulses which can be counted or, in the alternative, can be displayed as a bright spot on an oscilloscope or other monitor.

In our copending U.S. patent application Ser. No. 244,060, filed Mar. 13, 1981, entitled "METHOD FOR DETERMINING THE QUALITY OF LIGHT SCATTERING MATERIAL", now U.S. Pat. No. 4,391,524 issued July 5, 1983 we describe the use of apparatus described in our aforementioned patent to determine the relative quality of wafers compared to each other or to a reference standard. The crystalline or structural quality of the material is determined by adjusting the threshold of intensity of detected scattered light so that the display of the detected signal on a visual display is sufficient to provide a full or "blossom" display of the device. The value of the threshold adjustment is a direct measurement of the crystalline or structural quality of the material. When the surface of the material being examined includes a pattern such as that found on patterned wafers, or indeed on any surface that has a diffraction grating pattern, such as a grooved video disc, the diffracted beams mix with the scattered signals to make it difficult, if not impossible, to determine defects and dust on the surface or indeed to determine the crystalline or structural quality of the material.

SUMMARY OF THE INVENTION

According to the present invention, surfaces having patterns with diffractive elements are scanned to develop scattered light for detection and evaluation. Specular reflections from the surface as well as diffracted beams from the patterns are blocked so that the detector is exposed to substantialy only diffusely scattered light.

DETAILED DESCRIPTION OF THE PREFERRED EMBODIMENTS

The detailed description to follow shall make reference to the drawing which comprises.

Figure 1:
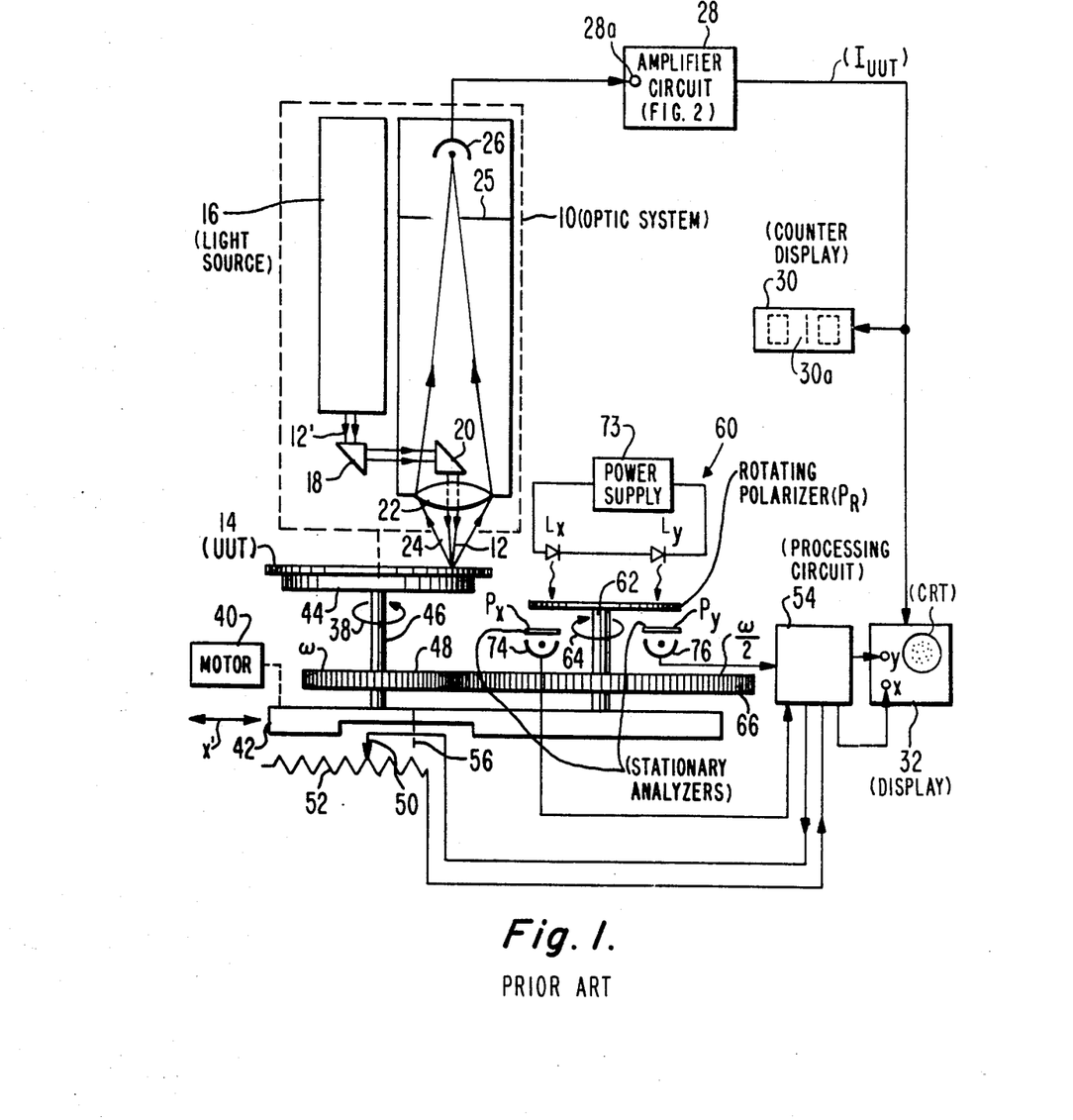
FIG. 1 which is a schematic of a prior art optical scanner apparatus useful in practicing the present invention.

Before proceeding to a detailed description of the method and apparatus of the present invention for detecting defects and dust on patterned surfaces such as a patterned wafer, reference is made to FIG. 1 illustrating a suitable optical scanner for practicing the present invention. The apparatus shown in FIG. 1 and described in detail in the above-identified U.S. Pat. No. 4,314,763 of Steigmeier et al. incorporated herein by reference, comprises an optical system 10 which includes a light source 16 providing a beam of light 12' passing through a series of prisms 18 and 20 and then through a focusing means, such as lens 22, forming beam 12. The light source 16 provides a light of any selected wavelength and includes light in the infrared (IR), visible or ultraviolet (UV) light spectrum. Light source 16 may be a low power laser, for example, a HeNe laser producing light at 6323 angstroms in wavelength which is focused by lens 22 into a spot 250 $\mu$m in diameter. For optimized conditions (of minimum beam spot size) elliptical spot sizes of 40 $\mu$m by 250 $\mu$m may be produced by inserting an appropriate cylindrical/spherical lens system (not shown) in between the two prisms 18 and 20. Beam 12 of the laser light is projected onto the surface 14 of an object such as the unit under test (UUT). The unit under test may be a wafer of silicon as used in the manufacture of integrated circuits (IC) and other semiconductor devices. Preferably the UUT is a wafer of silicon on sapphire (SOS). However, wafers of epitaxial deposited silicon on substrates such as silicon, spinel, etc., may be used in the use of such a scanner. Moreover, the quality of dielectric material and of amorphous or polycrystalline silicon material may also be determined.

The position of the light source 16 is not critical, but the position of the beam 12 between the prism 20 and object surface is important. The axis of the beam is substantially perpendicular to the surface 14. Light generated by laser 16 is scanned over the surface 14 of the UUT and is reflected back through the lens 22 via beam pattern 24 and collected on a photodetector 26 which is positioned along the axis of the beam 12. Lens 22 in combination with prism 20 serves as a first of two spatial filters to specular reflected light along the axis of beam 12. The defects that appear on the surface 14 of UUT may be as small as 0.3 to 1 μm in area. A defect may extend beyond the diameter of the laser beam, namely beyond 250 μm, in which case its shape, as distinguished from its mere size, will be detected by the scanning process. Surface defects scatter a sufficient amount of light beyond prism 20 so as to be detected by photodetector 26. In general, since an ideally optically flat surface will not scatter light, (apart from the very low amount of intrinsic light scattering resulting from entropy/temperature fluctuations which is of no relevance to the present invention), the defect will have surface portions that are not optically flat with respect to the incident light.

Figure 2:
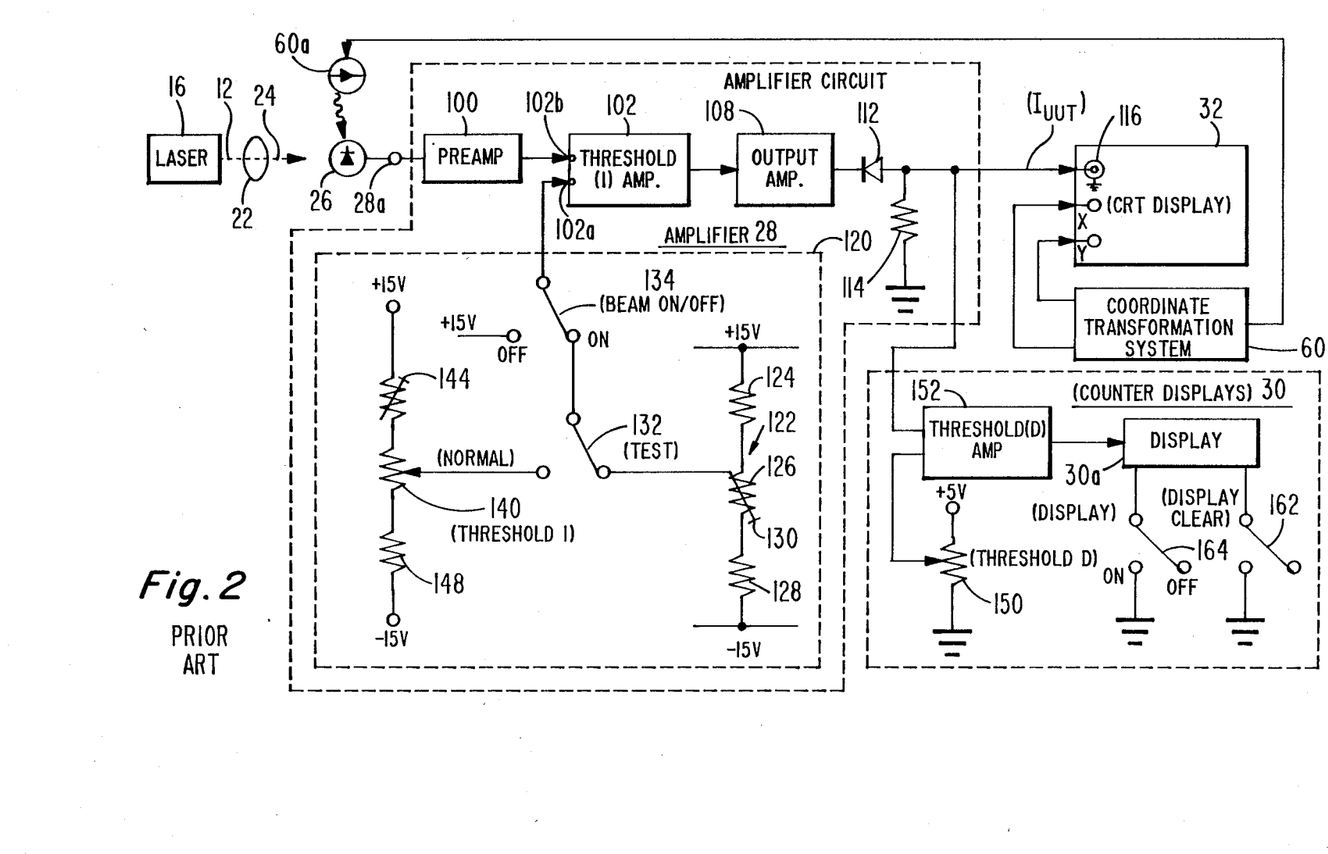
FIG. 2 which is a block schematic of the prior art amplifier circuit of the scanner illustrated in FIG. 1.

An aperture mask 25 acts as the second spatial filter in optical system 10 and prevents ambient light from being projected onto the detector 26. The output of detector 26 is applied to an amplifier circuit 28 which provides an output signal to either or both a counter display 30 or a cathode ray tube (CRT) display 32. Counter display 30 counts the number of defects that are detected during a scan of beam 12. The CRT display 32 provides a visual display of the relative spatial distributions of the locations of the defects on the UUT. Amplifier 28 is a high gain amplifier analogue in nature and produces an amplified output of the detector output with respect to the input signal it receives from detector 26 at terminal 28a. This results in gray scale in the CRT display 32, the intensity of the indications of defects on the CRT screen being indicative of the defects. A more detailed schematic of amplifier 28 is shown in FIG. 2 to be described.

In the form of the scanner shown in FIG. 1, the beam 12 scans the UUT in spiral fashion and the electron beam of the display 32 is also scanned in spiral fashion. The UUT may be a circular surface and for such purposes a spiral pattern is useful. For square shaped surfaces a circular inscribed portion is scanned. If desired, the pattern may be converted into an X-Y display which is achieved by the coordinate transformation system 60 which transforms polar coordinates of the beam striking at surface 14 into suitable rectangular coordinates which are applied as X-Y coordinate inputs for the display 32. A detailed description of the polar coordinate system is not given here, but a more detailed description is given of this and other features of a laser scanner in the above-identified U.S. Pat. No. 4,314,763 described above and incorporated by reference hereby. In brief, the coordinate system 60 includes a polarizer $P_R$, spaced, stationary analyzers $P_y$ and $P_x$, and detectors 74 and 76 excited by the light emitting photodiodes $L_x$ and $L_y$, which are energized by power supply 73. The system 60 includes a shaft 62 rotating in direction 64 over rotatable table support 42 slideable by motor 40. A gear 66 connected to shaft 62 is meshed with gear 48 so that the polarizer $P_R$ rotates at a predetermined angular speed, typically one half the angular speed of the UUT on table 44 rotated by shaft 46 in direction 38. The light from the diodes $L_x$ and $L_y$ are passed through the polarizer $P_R$ and detected by detector 74 and 76 and applied to the processing circuit 54. A wiper arm 50 is connected (dashed line 56) to the table 42 and moves with the table 42 as the table translates in the direction x'. The wiper arm 50 is part of a potentiometer 52 which is connected to processing circuit 54 for position control purposes. The processing circuit 54 provides the X and Y signals for application to the CRT 32 in the manner described in the above-identified patent.

In operation, when the incident beam 12 is positioned at the center of the UUT, the output of amplifier 28 is zero. As the beam 12 is moved from the center, signals are detected by detector 26 and applied to amplifier circuit 28 and applied to display 32. The display is scanned in an X-Y direction, providing a visual display corresponding to the scattered light from the beam 12. The display appears as bright spots and positions of the spots on the display screen correspond to the spatial distribution of the locations of the defects on or close to the surface of the UUT.

The unit under test (UUT) used in the laser scanning apparatus of FIG. 1 is typically an unpatterned wafer. However, as wafers are processed in the manufacture of IC devices, more or less involved patterns are developed on the wafer. The problem of inspecting such wafers for dust and defects is a vital concern. In the use of the scanning apparatus described hereinabove, a difficult problem arises in that the scattered light from the surface of the wafers having patterns cause erroneous signals since diffracted beams interfere with the scattered reflections.

Figure 4:
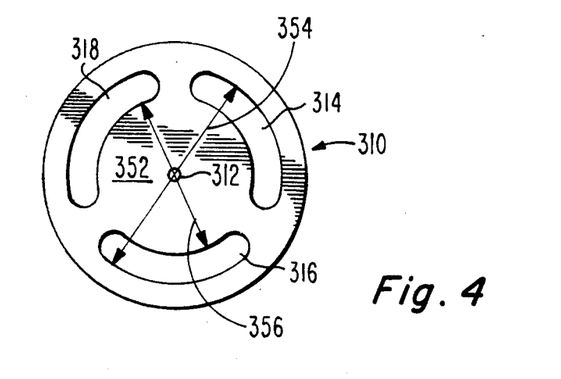
FIG. 4 is the mask illustrated in FIG. 3 as seen along viewing plane 4—4.

According to the present invention, a mask such as mask 310 shown in FIG. 4 to be described in greater detail hereinafter is used to selectively pass only scattered light and to block both specular reflections and diffracted light beams. The principle of the design of the mask 310 is based on the diffraction law:

$$\sin\alpha = n\lambda/d \quad (1)$$

where $\alpha$ is the angle between an incident beam and the first order diffracted beam, n is the order of the diffracted beam which is one for the first order beam, d is the periodicity, that is, the dimension of the diffracting grating-like elements of a wafer and $\lambda$ is the wavelength of the illuminating light. Using equation (1) in a typical scanning operation of a wafer having patterned dimensions containing spaced lines in a substantially orthogonal relationship of about 3 μm, light at 4416 angstroms, the angle $\alpha$ is about 8.5° for first order diffraction beams. The diffracted beams of lower orders, as well as some higher diffracted order beams, that could mix with scattered reflections must be blocked, in order to reduce the unwanted diffracted light and to thereby allow the scanning apparatus to observe only scattered light which will manifest defects and dust on the surfaces.

Laser beams of other wavelengths are also useful depending on the configuration of the patterns being scanned. Thus, laser beams with wavelengths at 3250 and 6328 angstroms may be used. The presently known useful range of wavelengths appears to be within 2600 to 6500 angstroms. Particularly useful beams have wavelengths selected from 3250, 4416, 4880 and 5145 angstroms.

Figure 3:
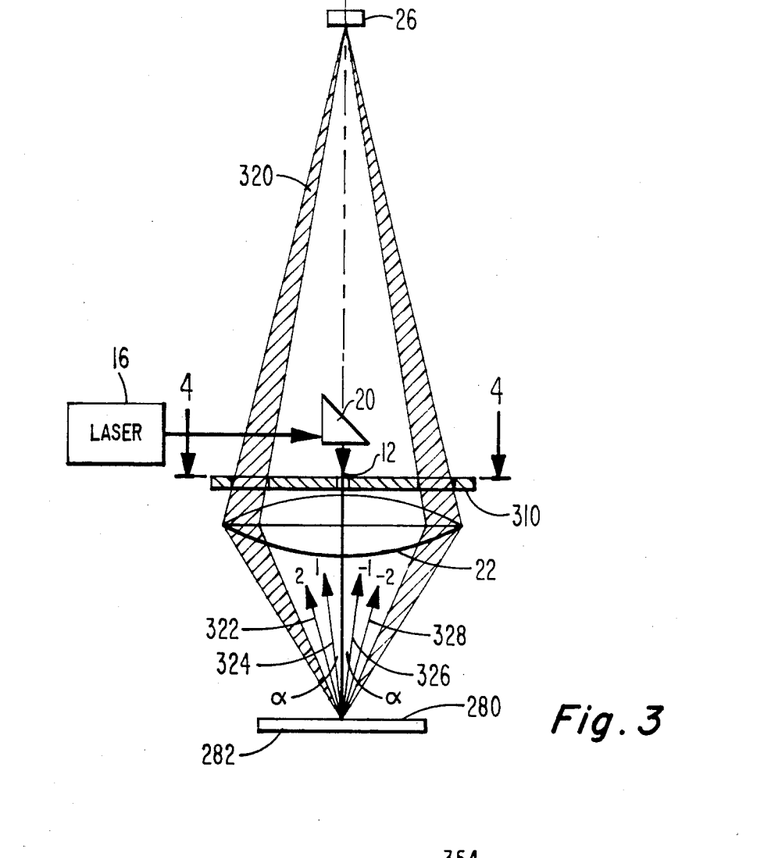
FIG. 3 is a schematic of a modification of the scanner illustrating the preferred embodiment of the invention.

A mask that provides these functions is arranged in the apparatus of FIG. 1 in the manner indicated in FIG. 3. A mask 310 generally circular formed of an opaque material, such as anodized aluminum, is positioned above the camera lens 22 illustrated in FIG. 1. The mask 310 is suitably positioned adjacent the lens surface or if desired may be positioned below the lens surface to be positioned thereby between the lens and the UUT, in this case a patterned wafer 282. Mask 310 has a central aperture 312 and three arcuate apertures 314, 316 and 318 passing light at angles with respect to the normal to surface 280 of wafer 282 between 14.6° to 15.8° for a lens of F/1.4 or preferably between 17° and 18.3° for a lens of F/1.2. The angles selected should preferably be considerably larger than the angles of the first order diffracted beam, relative to the incident light. The larger the angle for a given angle difference, the better. Therefore, the smaller the f-number of the lens, the better. Thus a lens of F/1.2 or larger aperture is preferred over one of F/1.4 since a larger central portion of the diffracted light can be blocked from the former. The radial dimensions of the arcuate apertures are selected to pass the annulus 320 of scattered light for focusing on photodetector 26 between these angles. The diffracted beams 324, 322, representing the first and second order diffracted beams and the diffracted beams 326 and 328 representing the arbitrarily designated negative first and second order diffractive beams respectively are spatially positioned about the incident light beam 12 from laser source 16 by an angle. In the illustration being described, $\alpha$ is the angle between the incident beam 12 and the first order diffracted beam 324. For a beam perpendicular to the surface $\alpha$ will also be the angle to the negative first order diffracted beam 326.

Thus, in operation, the laser 16 provides a beam 12 deflected by a mirror or preferably the prism 20 through aperture 312 of the mask 310 passing through the camera lens 22 and thence to the surface 280 of the patterned wafer 282. Specular reflections will return on the path of the incident beam 12 and through the aperture 312 but will be prevented from reaching the detector by prism 20. Some of the scattered light from the surface is focused by the lens 22 into an annulus 320 of scattered light passing through the apertures 314, 316 and 318 and focused on the detector 26. Diffracted beams 322, 324, 326, 328, etc. are blocked from detector 26 by the opaque portion 352 of the mask 310. Thus, the unwanted light diffracted from the regular arranged parts of a wafer pattern is blocked by the center portion 352 up to some one half aperture angle, generally 10° or more, from reaching the detector 26. Thus concentric arcuate apertures 314, 316 and 318 properly positioned permit only the light scattered from defects and dust on the surface to pass to the detector.

The principle of design for the apertures in the mask 310 is that the maximum diameter of the apertures of the device must be larger than the maximum aperture of the lens 22. The minimum diameter of the aperture of the arcs must be at least large enough to block the first order of diffracted beams. The maximum diameter is shown in FIG. 4 by the diameter dimensional line 354. Similarly, the minimum diameter line is indicated by line 356.

Before describing several examples of patterns of scattered light that were made according to the invention reference is made to FIG. 2 shown and described in greater detail in the aforementioned co-pending application Ser. No. 244,060, now U.S. Pat. No. 4,391,524, issued July 5, 1983. FIG. 2 is a simplified version of the amplifier circuit 28 but still showing its relation to other portions of the scanner system. Laser 16 as previously described provides a fixed intensity beam 12 which is scattered as beam 24 which, in turn, is detected by detector 26. The output of detector 26 is coupled via terminal 28a to a preamplifier 100 which in turn is coupled to a threshold voltage amplifier 102 and thence to an output amplifier 108 and a diode 112. Output resistor 114 (connected to ground) provides the output signal which is applied to the cathode of the CRT 32, as at terminal 116.

A threshold control network 120 provides a means for controlling to a predetermined or preselected value the intensity I of the beam of the CRT display 32. The network 120 comprises for testing a reference potentiometer 122 formed of serial resistors 124, 126 and 128 connected between +15 volts and −15 volts. An adjustment tap 130 is connected to one terminal of a single pole, double throw switch 132, the common terminal of which is connected to another switch 134 and thence to the input 102a of "threshold amplifier" 102. This network 120 provides in a test mode an adjustable voltage to the threshold (I) amplifier 102 to provide a suitable test signal for display on the CRT display 32 for alignment amplifier testing purposes, etc. Threshold amplifier 102 is a suitable operational amplifier having a first input 102b and a second input 102a. The network 120 with the switches 132 and 134 in the position as shown provides a control voltage to terminal 102a of amplifier 102 as the test mode of operation during which the laser is scanning the UUT or wafer. In this test mode a light emitting diode 60a is triggered by the coordinate transformation system 60 to flash light pulses four times per revolution of the wafer UUT (14) at the detector 26. The output signal of detector 26 after amplification through preamplifier 100 and amplifier 102 and 108 produces a test pattern on the CRT display 32 for judging the good alignment values of the optics and the good working condition of the electronics.

For "normal" operation to preset the predetermined threshold at which the CRT beam provides a predetermined intensity I, a threshold intensity adjustment potentiometer 140 is connected between resistors 144 and 148 in turn connected to +15 volts and −15 volts. The resistors can be selected to provide different voltage ranges to change the intensity of the CRT beam over a range of values as desired.

In operation, with switches 134 and 132 positioned to the "normal" position, i.e. in a position opposite to that shown in FIG. 2, the intensity threshold (I) control 140 will be in the circuit. By adjusting potentiometer 140, the intensity (I) of the CRT beam may be adjusted to a predetermined value. Suitable calibration indicia for example, "0" to "1000" on the potentiometer may be provided (not shown) as a repeatable reference of the selected position of the potentiometer 140.

In addition to the threshold (I) intensity control network 120, a second threshold (D) control 150 is provided to modify the intensity signal ($I_{UUT}$) for counter display 30. The D threshold adjustment 150 provides a reference adjustment of a threshold amplifier 152 whose output is coupled to counter 30a of display 30 shown in FIG. 1. With contact switch 162 normally open in the position shown, triggered events will be registered in the display 30 and with the switch 162 operated momentarily to the closed position to ground the display 30 is cleared to "0000." Switch 164 is a switch for controlling the CRT beam to be on or off according to the switch positions as shown. The coordinate transformation system 60, described above for FIG. 1, as shown in block form is coupled to terminals X and Y of the CRT scope display 32 to provide a signal for controlling the X-Y display pattern described above.

Thus, the threshold intensity (I) potentiometer 140 and threshold (D) potentiometer 150 provide an adjustable detection sensitivity control of the scattered light for the CRT 32 display and the counter display 30, respectively. The sensitivity of detection can be further changed by increasing the gain of the preamplifier 100 and the amplifier 108 or by inserting an attenuator of suitable value (not shown) between the two. The intensity of the CRT display beam is adjusted by the threshold (I) potentiometer 140 to increase the detector signal sufficiently to the level at which the CRT 32 displays the detected signal.

Figure 6:
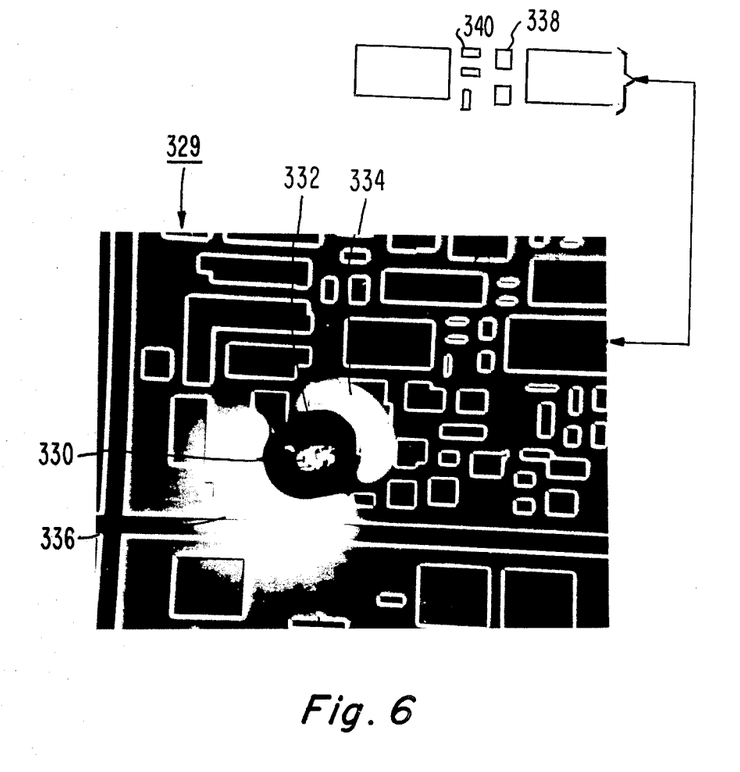
FIG. 6 is a microphotograph of a patterned silicon wafer showing a defect that is detected according to the present invention.

With a UUT in position on the table 44, the scanner provides a beam 12 which in turn results in a scattered beam 24 which will, after detection, provide a display on CRT 32. Defects that may appear will be counted in the typical prior art procedures on counter display 30 and displayed on the CRT. Thus, in the prior art operation of the scanner apparatus, defects on the surface of an object of semiconductor material are detected by scanning the surface and adjusting the potentiometer 140 of the threshold (I) control (FIG. 2) at various values to provide a visual display on the CRT of display 32 or a count of defects on counter display 30 as described in detail in the aforementioned Steigmeier, et al. patent application and patent. The particular size of a defect can be identified by calibrations of setting of the threshold (I) potentiometer 140 and/or threshold (D) potentiometer 150. The laser scanner with the capability of the threshold I potentiometer 140 allows for a scattering analysis to identify or detect dust and scratches and other defects on the surface of the patterned wafer provided the mask 310 of FIG. 3 is used. For example, a photomicrograph of a patterned silicon wafer 329 as shown in FIG. 6 has a defect in the form of a protrusion 330. The dark portion 332 surrounding the protrusion 330 is an artifact caused by the optical effects of the incident light in taking the photograph. The white portions 334 and 336 are also artifacts due to other problems of illumination. It is known from other microscopic evaluations that the defect is solely the protrusion 330.

The average dimension of the pattern elements acting as grating elements such as the edges (both short and long) of devices 338 or 340, as shown in the line sketch above the photomicrograph keyed by the double arrowed line, are typically 5 to 10 μm (estimated) for the pattern of FIG. 6. In present day devices the typical pattern elements acting as grating elements may be of the order of 3 μm, decreasing in future devices to typically 2 or 1 μm. Note that it is not the average distance between various devices which matters, but the smallest typical pattern dimensions, like edges, individual lines, etc. It is evident that there is a regular orthogonal array of lines on wafer 329 (FIG. 6) that appears as a diffraction grating pattern. When the surface of the patterned wafer 329 is exposed to the laser beam 12, as in FIG. 3, wafer 329 replacing wafer 280, the pattern generates diffracted light beams that indeed follow diffraction principles. The angle α of the diffracted beams are, in practice, determined by the actual pattern under study. The size of the apertures 314, 316 and 318 are thus determined by the pattern to be studied. A different diffraction pattern will be generated by a differently patterned wafer than the one shown in FIG. 6. However, we have discovered that a mask 310 designed for a particular patterned wafer such as wafer 329 (FIG. 6) will be adequate to provide an acceptable mask for patterned wafers of different configuration meeting however the requirements for the grating-like elements of about 2 μm and larger.

Figure 7A:
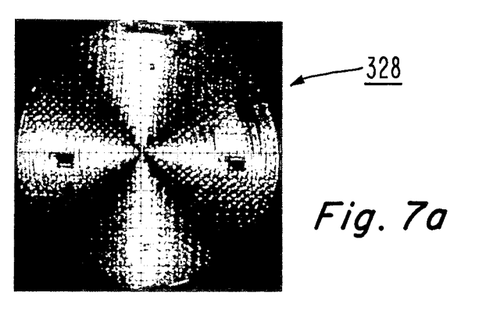
FIGS. 7a, 7b and 7c are photographs of the scanner display of a surface of a patterned wafer without the mask of the invention of three different specimen wafers.
Figure 8A:
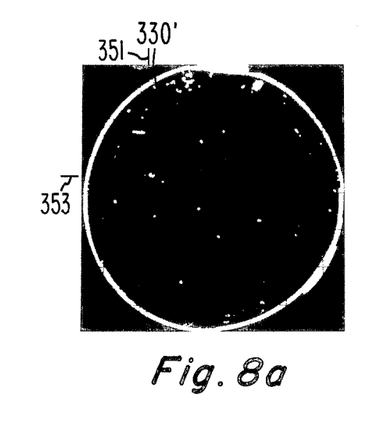
FIGS. 8a, 8b and 8c are photographs of the scanned display of the same wafers used in FIGS. 7a–7c, respectively, but with the mask of the invention.
Figure 8B:
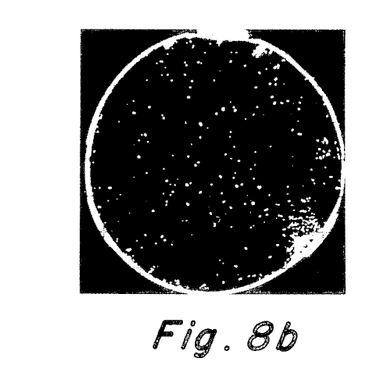
Figure 8C:
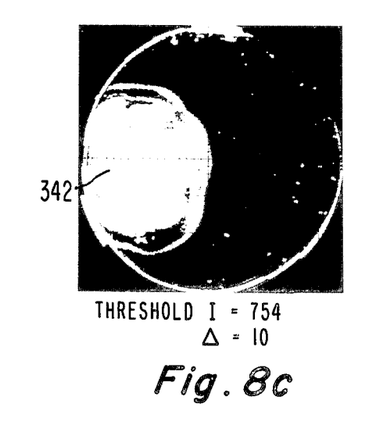
Figure 9A:
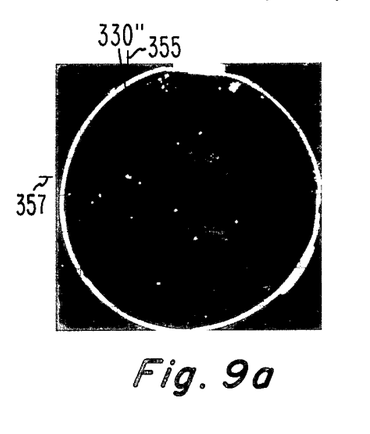
FIGS. 9a–9c are photographs corresponding to FIGS. 8a–8c, respectively, but with a different threshold setting for the display.

Patterned wafer 329 was positioned on the apparatus of FIG. 3 and moved to effect a scanning of the beam 12 over the surface thereof. The mask 310 was removed so that the diffracted beams 322, etc. were not blocked and were allowed thus to mix with the scattered light annulus 320. FIG. 7a is a photomicrograph of that scan displaying what appears to be a "Maltese cross." The sensitivity of threshold I was set at "000" units and an attenuator of 30 dB was inserted between preamplifier 100 and amplifier 102 of FIG. 2. The mask 310 was then positioned into the scanning apparatus of FIG. 3 and a scan was made wherein the threshold I potentiometer was adjusted to an arbitrary value of 754 and at the same time the gain was increased by removing the above mentioned 30 dB attenuator. The threshold value of 754 is a difference or Δ of 10 units below the full threshold value at which the CRT display exhibits full writing. We call this either the "full" value or the "blossom" threshold I value. It is seen that the "Maltese cross" appearing in FIG. 7a does not appear in FIG. 8a. The "Maltese Cross" of FIGS. 7a-7c being nothing else but the diffraction pattern produced by the grating-like elements in the patterned wafer, is avoided in FIGS. 8a-8c. Instead we can now, at a much higher sensitivity level even, detect many scattering events (from dust, defects, etc.) which before were superceded by the "Maltese Cross" intensity. Moreover, the defect 330 of FIG. 6 was correlated to photomicrograph of FIG. 8a in which the defect is identified by the lead line 330'. To help the reader locate the defect in the photographs of FIG. 8a, lines 351 and 353 are drawn as the x and y coordinate extensions from that defect on FIG. 8a. Another scan was taken of the same wafer 328 but this time with the threshold I potentiometer 140 set at a value of 704. The photomicrograph of this scan, which accounts for the lower sensitivity than for that in FIG. 8a, is as shown in FIG. 9a. The difference Δ of 60 was used as compared to a Δ of 10 for FIG. 8a amounting to lower sensitivity. The most pronounced events are again observed and the defect corresponding to defect 330 of FIG. 6 is indicated as 330". X and y extension lines 355 and 357, similarly as in FIG. 8a, are drawn from the defect 330" in FIG. 9a.

To make the photograph of FIG. 7a, the amplifier 28 of the apparatus was provided with a 30 db attenuator to cut down the gain and a low threshold I potentiometer 140 setting of an arbitrary value of 000 units. This operation results in the diffraction patterns manifested as the "Maltese cross" shown in FIG. 7a. Only extremely strong defects or dust would show up at such a low gain and even they would be difficult to observe due to the strong diffraction beams mixed with the scattered light. For the photographs of FIGS. 8a and 9a with the mask 310 of the invention inserted in the amplifier 28 of the apparatus, a high gain was used having a 0 db attenuation. It is seen that a high number of defects, and possibly dust events, are seen in the micrographs of FIGS. 8a and 9a. FIGS. 8a and 9a as indicated above, are a result of two respective different sensitivity (I) settings in which Δ=10 is more sensitive than Δ=60 which, in turn, is less sensitive. Thus, Δ is defined as the difference between the full or "blossom" threshold I potentiometer 140 value of 764 units and the actual I value of 754 or 704 units, respectively. FIG. 8a shows more details for a setting at which Δ=10 units. Nevertheless, other threshold settings can be also chosen according to the size and scatterinq efficiency of the defects and to the needs of detection sensitivity for a particular application.

Figure 7B:
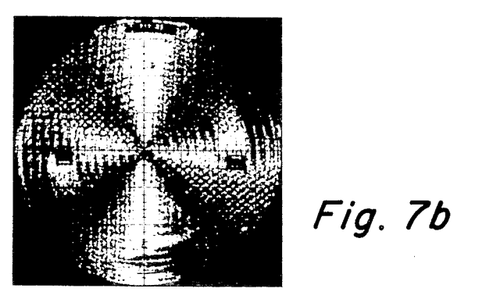
Figure 7C:
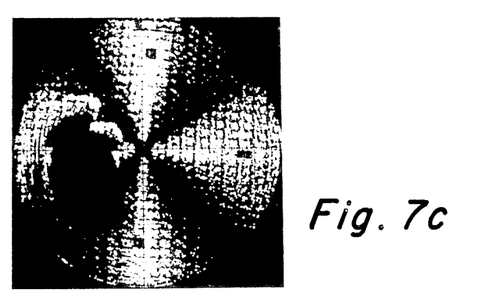

FIGS. 7b and 7c are additional examples of patterned wafers of different configuration than that of wafer 328 shown in FIG. 6 without the mask 310 in position. The "Maltese cross" is seen in both of them.

Figure 9B:
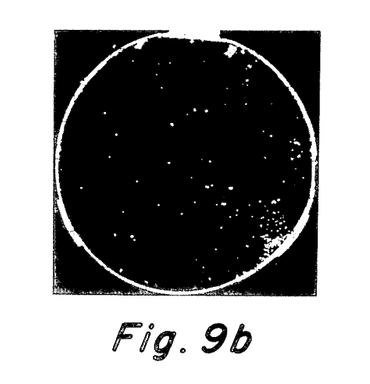
Figure 9C:
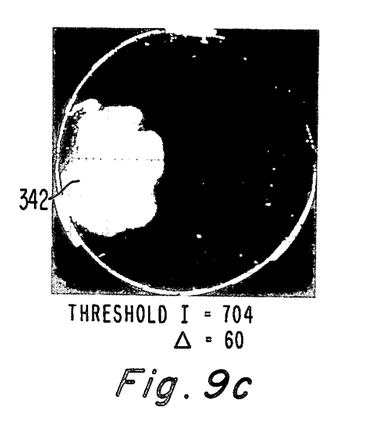

The same wafers are then scanned with the mask 310 in position and with the same threshold I potentiometer adjustments as that used for wafer 328 and again with the 30 dB attenuator removed. FIGS. 8b, 8c and 9b and 9c represent those scans, respectively. It will be noticed that the photograph of FIG. 9c shows stain masks represented by the white portion 342. This stain 342 cannot be detected by the scan of the same wafer without the mask 310 in position as shown by the micrograph of FIG. 7c which displays essentially only the "Maltese cross."

If desired, one can provide with the scanning apparatus of FIG. 3 a microscope attachment which can be used to provide a 1:1 correlation of scattering events whether caused by defects or dust. This procedure allows one to identify the defect on the patterned wafer visually and inspect it.

While the preferred embodiment of the invention utilizes the scanning apparatus in which the laser beam 12 is directed to the surface of the UUT to be scanned, substantially perpendicularly, an alternative approach may be used in which the incident laser beam 12 is directed to the surface of the UUT at an oblique angle such that the low diffraction order beams of the first and second order, for example, produced by the rather regular wafer patterns elements, will fall outside the collection aperture of the lens 22. Such a mode of operation may not require a mask of the type illustrated in FIG. 4. However, it requires a mask of a different configuration with the blocking parts on the outer portions of the scattered light aperture. Such a mask is illustrated in FIG. 5.

Figure 5:
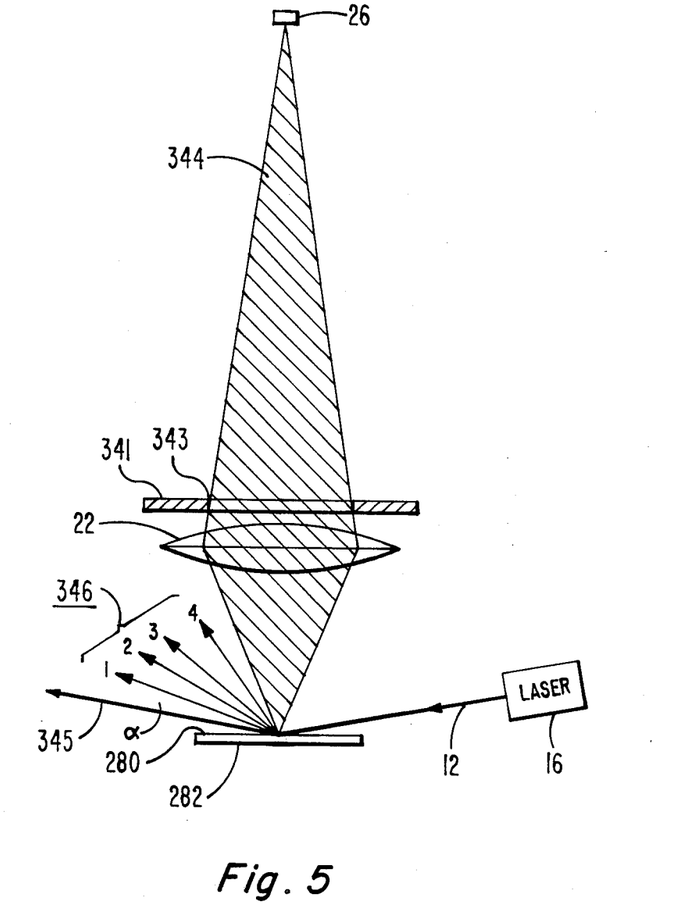
FIG. 5 is a schematic of a modification of the embodiment as shown in FIG. 3 showing an alternative but not a preferred form of the invention.

As shown in FIG. 5, a mask 341 is positioned in the apparatus to receive scattered light 344 from the surface 280 for focusing by lens 22 on detector 26. In order to generate such a pattern, the laser 16 provides beam 12 at an oblique angle via a mirror or prism not shown. The specularly reflected beam 345 is reflected as shown according to conventional specular optics. Scattered light will be generated and some of it will be focused by lens 22 through aperture 343 of the mask 341. The diffracted beam 346 of different orders will be diffracted along the paths shown.

The invention as described hereinabove has been directed to scan a patterned wafer. It appears that the invention may also be practiced on surfaces such as that provided by a grooved video disc. The scanning laser of FIG. 1 as modified by the arrangement for the mask 310 as shown in FIG. 3 may be utilized in the practice of the invention on a grooved video disc. See the RCA CED Video Disc System—An Overview by J. J. Brandinger, pp. 333–343, RCA Review, Sept. 1981, Vol. 42, No. 3 for a description of the composition and manufacture of a video disc.

Experiments have been performed using a fragment of a grooved video disc. The invention can also be practiced, it will be understood, to scan an entire video disc with appropriate design of the apparatus. The form of the mask needed to scan a video disc does not differ from what has been described above. Since the grating-like features in the video disc are given by the grooves, and the even finer video information recorded within the grooves, a stronger diffraction is to be expected, i.e., larger angles of the diffracted beams. It is, therefore, more difficult to achieve the same good results as for patterned wafers, and, although the f/1.4 lens and angles between 14.6 and 15.8 degrees produced convincing results, one might have to use angles of 17° to 18.3° as described hereinabove in the description of FIG. 3.

Figure 10A:
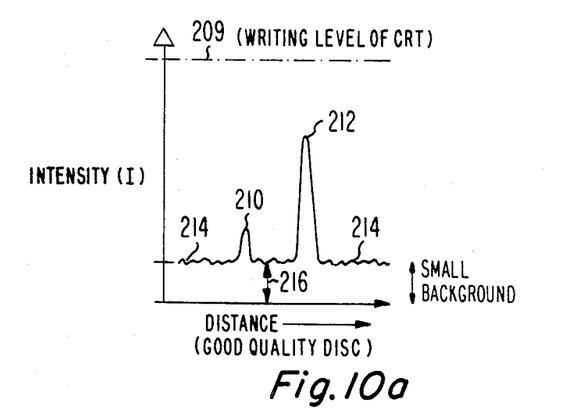
FIGS. 10a and 10b respectively are curve plots useful in understanding one aspect of the invention wherein the detected scattering signals of two different specimens of different quality are scanned.
Figure 10B:
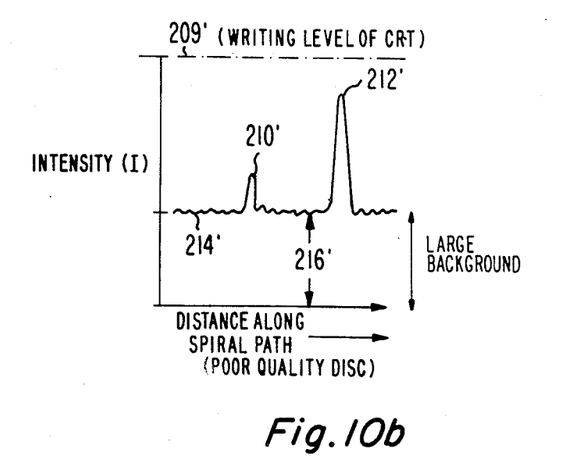

We have demonstrated the use of the scanning laser in the mode of determining the quality of the bulk material as described in the aforementioned copending application Ser. No. 244,060. On an unembossed, (i.e., a non-grooved) video disc, we have shown a great number of scattering centers which appear to be related to the material composition due to local changes in the composition in the material. These scattering centers cannot be accounted by a few dust particles, for example, on the surface. Moreover, we have determined that the material quality of the unembossed video disc as measured by the blossom or full threshold I at setting 140 is different for different unembossed discs and aso varies across a particular disc. This blossom or full threshold I setting is what we have termed the quality control use mode of the apparatus of the invention as described in our aforementioned copending application. That mode of operation is illustrated in FIGS. 10a and 10b. The full intensity setting (blossom) occurs with level 214 adjusted to be at level 209 in FIG. 10a or with level 214' at level 209' in FIG. 10b. The quality of two different wafers as explained in the copending application or in the present instance of video discs can be represented by the difference in the background of the threshold value of the scanned signal. Thus, the distance 216 of FIG. 10a representing a small background is indicative of a good quality wafer or video disc. A large background as represented by the distance 216 as shown in FIG. 10b is indicative of a poor quality wafer or disc.

We have discovered that the mask 310 can be used to determine the quality of a video disc using the quality control mode of the apparatus briefly summarized above and represented by FIGS. 10a and 10b. In the practice of the invention using a video disc, we have inspected video disc material with embossed grooves without interference from the very high level of diffracted light that originates not only from the periodic structure of the embossed grooves but also from the video information on the video disc. Photographs made of such scans were very similar to those taken of patterned wafers as shown in FIGS. 7 to 9.

The invention can be practiced in the stationary mode by mainly positioning the beam 12 on the wafer by rotating the table by hand. In practice, the apparatus shown in FIG. 1 would be modified to use a simple table at the place of the UUT on which the wafer or video disc can be placed. Alternatively, a simple stage may be provided which is arranged to select five representative locations on which tests could be made successively. This would provide a simpler and faster technique than scanning the entire surface and would provide a simpler technique for making an easier evaluation of the wafer or disc on the selected spots. However, the overall quality of the wafer or disc would be unknown in fact.

While any form of laser light may be used in the practice of the invention (e.g., light within wavelengths of 2,600–5,200 angstroms and up to 6500 angstroms for video discs), it has been discovered that epitaxial layers of SOS wafers and other thin layer materials are somewhat transparent to blue laser light and quite transparent to red light. As a result, some interference stripes have been observed in the areas of SOS wafers that are close to but not at the threshold value of potentiometer 140 to develop a full display. In the preferred form of practicing the invention, an ultraviolet laser light is used. An ultraviolet laser light has been discovered to virtually eliminate the undesirable stripes found in the use of blue laser light. While the mask of the embodiments of the invention described utilize apertures to pass the scattered and incident light, a solid opaque disc having transparent portions may be used.

Moreover, the invention can be used to determine defects and dust in all kinds of patterned wafers, for example, photomasks, or E-Beam masks after writing or processing, CCD Wafers, and the diode array side of silicon vidicon targets. Wafers with metal coatings, even if only partly coated, will be difficult to scan since the resulting diffused scattering can be quite high, i.e., high contrast of the metallic surface causes much diffused scattering. The bulk property of a patterned wafer can, in principle, be used. However, in practice, most patterned wafers are sold with bulk portions consisting of different regions of different "bulk" quality. For that reason, determining the quality of such wafers would not particularly useful with this invention.

What is claimed is:

1. In an apparatus of the type for optically detecting microscopic defects in a certain specularly reflecting surface of a given object, said surface having at least on a portion thereof a diffraction grating pattern or at least some elements of a diffraction grating pattern capable of diffracting said beam of light into diffracted beams of various orders, said apparatus comprising first means for scanning said reflecting surface with an incident beam of light that illuminates a relatively small spot area of said entire reflecting surface area, which spot area is large relative to the area of any microscopic defect, the incident beam of light being directed to said surface such that a substantial amount of light scattered from the surface illuminated by the incident beam of light is detected substantially independently of light specularly reflected from the same surface, and a second means for varying the threshold of detection of the scattered light, the improvement characterized by:

means comprising a disc member positioned in said apparatus between said surface and said detector and having a central aperture with a diameter sufficient to pass a substantial amount of said scattered light, the incident beam of light being directed to said surface at an angle such that diffracted beams of low diffraction orders do not pass through said central aperture.

2. The apparatus of claim 1 wherein said incident light beam is a laser beam having a wavelength selected from the group consisting of 3250, 4416, 4880, 5145 and 6328 angstroms, and the diffraction pattern on said surface is a device pattern on a semiconductor wafer including diffraction dimensions on the order of 1.5 to 10 micrometers.

3. A method for optically detecting dust and defects on an object surface having surface portions with diffraction grating patterns or at least some elements of a diffraction grating pattern, comprising the steps of:

scanning said object surface with a beam of incident light having a given spot size, said beam being scanned at an oblique angle to said surface such that diffracted beams from said diffraction grating pattern are spread with lower order diffracted beams being more widely spaced from each other than the higher order diffracted beams and such that scattered light is confined to a cone between a higher order diffracted beam and the incident beam;

positioning a detector to detect a substantial amount of light scattered from said object surface illuminated by said scanning beam substantially independent of light specularly reflected from the same surface; and positioning an opaque disc having a central aperture to pass scattered light to said detector and to block diffracted light beams from said detector.

4. The method of claim 3 wherein said diffraction grating pattern is comprised of a grooved video disc, wherein said scanning step comprises:

(a) rotating at least a portion of said disc relative to a fixed incident light beam of a laser at a selected wavelength;

(b) positioning an opaque disc having an aperture to pass scattered light to said detector and to block diffracted beams from said detector;

(c) detecting scattered light to provide an adjustable electrical signal representing the intensity of the scattered light;

(d) applying the electrical signal to a visual display device to control the intensity of the display beam just sufficiently to provide a visual display representing light scattered from the video disc; and (e) varying the magnitude of the electrical signal to vary thereby the magnitude of the intensity of the display beam just sufficiently to provide a visual display representing light scattered from said video disc.

5. The method of claim 4 wherein the light exposing step comprises scanning the light beam of a selected surface portion of the video disc and wherein said varying step comprises varying the electrical signal just sufficiently to provide a visual display of the entire selected surface portion.

6. The method according to claim 4 wherein the light exposing step comprises exposing the beam to a plurality of selected spatially separated portions of the surface of the material.

7. The method according to claim 4 wherein the wavelength of said light is selected from a wavelength within the range of 2,600–6,500 angstroms.

8. The method according to claim 7 wherein said wavelength of light is selected from the group consisting of 3250, 4416, 4880, 5145 and 6328 angstroms.

* * * * *